(12) United States Patent
Forsell

(10) Patent No.: US 9,814,559 B1
(45) Date of Patent: Nov. 14, 2017

(54) MEDICAL IMPLANT APPARATUS WITH WIRELESS ENERGY TRANSMISSION

(76) Inventor: Peter Forsell, Zug (CH)

(*) Notice: Subject to any disclaimer, the term of this patent is extended or adjusted under 35 U.S.C. 154(b) by 3759 days.

(21) Appl. No.: 11/988,450

(22) PCT Filed: Aug. 1, 2000

(86) PCT No.: PCT/SE00/01528
§ 371 (c)(1),
(2), (4) Date: May 27, 2009

(87) PCT Pub. No.: WO01/12108
PCT Pub. Date: Feb. 22, 2001

Related U.S. Application Data

(60) Provisional application No. 60/148,345, filed on Aug. 12, 1999, provisional application No. 60/182,223, filed on Feb. 14, 2000.

(51) Int. Cl.
*A61F 2/02* (2006.01)

(52) U.S. Cl.
CPC ..................................... *A61F 2/02* (2013.01)

(58) Field of Classification Search
CPC .. A61B 5/0031; A61N 1/3702; A61N 1/3787; A61N 1/37205; A61N 1/08; A61N 1/378; A61N 2/37211
USPC ..................... 128/899; 600/517, 585; 607/33
See application file for complete search history.

(56) References Cited

U.S. PATENT DOCUMENTS

| 4,026,305 | A | | 5/1977 | Brownlee et al. |
| 4,032,363 | A | * | 6/1977 | Raag ....................... H01L 35/00 136/201 |
| 4,483,341 | A | * | 11/1984 | Witteles .......................... 606/21 |
| 4,692,147 | A | * | 9/1987 | Duggan ...................... 604/891.1 |
| 5,713,939 | A | * | 2/1998 | Nedungadi et al. ............. 607/33 |
| 6,129,685 | A | * | 10/2000 | Howard, III ................... 600/585 |
| 6,501,983 | B1 | * | 12/2002 | Natarajan et al. ............. 600/517 |

FOREIGN PATENT DOCUMENTS

| EP | 0 876 808 | 11/1998 |
| WO | 99/18885 | 4/1999 |
| WO | 00/09048 | 2/2000 |
| WO | 00/15158 | 3/2000 |

OTHER PUBLICATIONS

International Search Report dated Jul. 11, 2001, in International Application No. PCT/SE00/01528.
Publication No. EP 1568338A2, dated Aug. 31, 2005, for European Patent Application No. 05010107.0.
European Search Report, dated Sep. 14, 2006, for EP 05010107.0.
Examination Report, dated Nov. 4, 2008, in European Patent Application No. 05010107.0.

* cited by examiner

*Primary Examiner* — Christine H Matthews

(57) ABSTRACT

A medical implant apparatus includes or uses an energy transmission device for wireless transmission of energy of a first form from outside a patient's body. An implanted medical device is operable in response to energy of a second form different than the energy of the first form. An implanted energy transforming device transforms energy of the first form wirelessly transmitted by the energy transmission device into energy of the second form for use in the control and operation of the medical device.

103 Claims, 5 Drawing Sheets

MEDICAL IMPLANT APPARATUS WITH WIRELESS ENERGY TRANSMISSION

This application is the U.S. national phase of International Application No. PCT/SE2000/01528, filed 1 Aug. 2000, which designated the U.S. and claims the benefit to U.S. Provisional Application Nos. 60/148,345, filed 12 Aug. 1999, and 60/182,223, filed 14 Feb. 2000, the entire contents of each of which are hereby incorporated herein by reference.

The present invention relates to a medical implant apparatus for a patient.

The development of medical devices to be implanted in human beings or animals is currently very intensive resulting in increasingly sophisticated devices. Therefore, the implanted medical devices require increasingly amounts of energy, in order to operate as desired. Typically, implanted power sources, such as batteries, are employed for powering the prior art implant devices.

U.S. Pat. No. 4,408,607 discloses an electric power supply for providing electrical energy to a medical device comprising a capacitor as the power source. The capacitor is charged from outside the patient's body by the use of a primary winding external to the patient's body and an implanted secondary winding. Radio frequency energy is transmitted from the primary winding to the secondary winding.

U.S. Pat. No. 5,713,939 discloses a medical device comprising a rechargeable battery which is charged by means of electromagnetic induction between an external coil and an implanted coil.

In modern medicine, implanted medical devices are used to control physical functions. There is a need or desire for controlling, adjusting or changing the performance of the implanted medical devices, in order to alter physical or other functions. In many applications the medical device should also be capable of sending information to an external receiver. In addition, it should be possible to send back commands to the implanted medical device for any kind of action.

For example, an implanted pump used to give medical treatment may be an alternative to injections, which are unpleasant for many patients. Besides, injections always means a risk of infection. Also, medically trained people have to give the injections. The amount of medical substance given to the patient may be correlated to, for example, the result of any kind of bloodtest performed by the implanted medical device. After data information on such a bloodtest has been analyzed, commands can be sent to a pump regarding the kind of treatment to be given and when treatment is to be given. The data information may be analyzed by means implanted in the human body. There are a great number of prior art medical devices that use or would be improved by using electrical energy for controlling any function of them when implanted.

The object of the present invention is to provide a medical implant apparatus which permits efficient transmission of external energy in a non-invasive manner to an energy operated medical device implanted in a patient.

Accordingly, the present invention provides a medical implant apparatus for a patient, comprising an energy transmission means for wireless transmission of energy of a first from outside the patient's body; an implantable medical device operable in response to energy of a second form; and an implantable energy transforming means for transforming the energy of the first form wirelessly transmitted by the energy transmission means into energy of the second form, which is used for the operation of the medical device.

As a result, the advantage is achieved that the medical implant apparatus of the invention provides simple and effective energy transmission which ensures an extended and reliable functionality of the apparatus, possibly for the rest of the patient's natural life, and at least many years.

Preferably, the energy transforming means comprises at least one element having a positive region and a negative region and adapted to create an energy field between the positive and negative regions when exposed to the energy of the first form transmitted by the energy transmission means, so that the energy field produces the energy of the second form.

Alternatively, at least one semiconductor circuitry, transistor circuitry or microchip may be substituted for the element having a positive and a negative region. Such a semiconductor circuitry, transistor circuitry or microchip is adapted to create an energy field when exposed to the energy of the first form wirelessly transmitted by the energy transmission means, whereby the energy field provides the energy of the second form.

Advantageously, the medical device is directly operated with the energy of the second form, preferably in a non-magnetic and/or non-mechanical manner, as the energy transmission means transmits the energy of the first form. The medical device may be directly operated with the energy of the second form without externally touching subcutaneously implanted components of the apparatus. The advantage of directly using energy as it is transmitted is that the apparatus can be of a very simple design and the few components involved makes the apparatus extremely reliable.

The medical device may be non-inflatable, i.e. with no hydraulic or pneumatic fluid involved for the adjustments of the medical device. This eliminates problems with fluid leaking from the medical device.

In accordance with a preferred embodiment of the invention, the element comprises an electrical junction element, and the electrical junction element is capable of inducing an electric field between the positive and negative regions when exposed to the first form energy transmitted by the energy transmission means, whereby the second form energy comprises electric energy.

Consequently, the medical device suitably is electrically operated, whereby the positive and negative regions of the electrical junction element supply electric energy for the operation of the medical device. The apparatus suitably comprises implantable electric conductors connected to the positive and negative regions of the electrical junction element, whereby the electrical junction element is capable of supplying an electric current, such as a direct current, a pulsating direct current, a combination of a direct and pulsating direct current, an alternating current or a combination of a direct and alternating current, via the conductors. Furthermore, the electrical junction element may be capable of supplying a frequency, amplitude, or frequency and amplitude modulated analog, digital, or a combination of analog and digital signal, which is used in connection with control of the medical device.

The element, preferably in the form of an electrical semiconductor junction element, suitably forms a flat and thin sheet and has a volume of less than 2000 cm$^3$ to be suited for subcutaneous implantation, so that the electrical junction element can be located just behind the skin of the patient. The electrical junction element should be designed to generate an output current exceeding 1 μA when exposed to the energy of the first form transmitted by the energy transmission means. Of course, all the components of the energy transforming means including the electrical junction element to be in contact with the patient's body should be of a biocompatible material. Alternatively, it would be possible to implant the energy transforming means in the thorax or cephal region of the patient, or in an orifice of the patient's body and under the mucosa or intraluminar outside the mucosa of the orifice.

For in vitro appliances, a particular type of an electrical semiconductor junction element has been commonly used, namely a so called p-n (positive/negative) junction element, typically in the form of solar cells. A solar cell transforms solar energy in the form of visible light into electric energy in the form of direct current. For example, a p-n junction element may comprise two layers of semiconductor, one p-type (positive) and the other n-type (negative), sandwiched together to form a "p-n junction". This p-n junction induces an electric field across the element when absorbing quanta of light (photons).

To be more precise, the quanta of light transfer their energy to some of the semiconductor's electrons, which are then able to move about through the material. For each such negatively charged electron, a corresponding positive charge—a "hole"—is created. In an ordinary semiconductor, these electrons and holes recombine after a short time and their energy is wasted as heat. However, when the electrons and holes are swept across the p-n junction in opposite directions by the action of the electric field, the separation of charge induces a voltage across the p-n junction element. By connecting the p-n junction element to an external circuit, the electrons are able to flow thereby creating a current.

Surprisingly, it has been proved that although both the skin and subcutis absorb energy from an external light beam directed against the skin portion behind which a properly designed p-n junction element is located, the light energy transmitted through the skin can induce a current from the p-n junction element strong enough (minimum 1 µA) to enable the operation of the electrically operated medical device. Thus, a principal junction element is now for the first time used for use solely as energy source in in vivo applications. The apparatus according to the present invention is adapted for in vivo use with sensitivity, output level, and temperature functionality adapted to in vitro purposes.

However, the apparatus of the present invention is not limited to the use of visible light for the wireless transmission of energy. Thus, in accordance with a broad aspect of the invention, the energy transmission means transmits energy by at least one wireless signal, preferably containing radiant energy.

The wireless signal may comprises a wave signal, for example an electromagnetic wave signal, such as an infrared light signal, a visible light signal, an ultra violet light signal, a laser signal, a micro wave signal, a radio wave signal, an x-ray radiation signal, and a gamma radiation signal. Where applicable, one or more of the above signals may be combined. Alternatively, the wave signal may comprise a sound wave signal, such as an ultrasonic signal. Generally, the wireless signal may comprise a digital, analog or a digital and analog signal.

The energy of the first form transmitted by the energy transmission means may comprise an electric or magnetic field transmitted in pulses, for example digital pulses. Furthermore, the energy transforming means may transform the energy of the first form, which may comprise polarized energy, into a direct current, pulsating direct current, a combination of a direct and pulsating direct current, an alternating current or a combination of a direct and alternating current. Alternatively, the energy of the first form may comprise kinetic energy. The energy of the second form may comprise a frequency, amplitude or frequency and amplitude modulated analog, digital or combined analog and digital signal.

The apparatus may further comprise an implantable pulse generator for generating electrical pulses from the energy of the second form produced by the energy field created by the element having positive and negative regions.

In accordance with another embodiment of the invention, the apparatus comprises an implantable operation means for operating the medical device and a control device for controlling the operation means, wherein the element powers the operation means with the energy of the second form. The operation means preferably comprises a motor, for example an electric linear motor or an electric rotary motor which is controlled by the control device to rotate a desired number of revolutions. The electric motor may have electrically conductive parts made of plastics. Alternatively, the motor may comprise a hydraulic or pneumatic fluid motor, wherein the control device controls the fluid flow through the fluid motor. Motors currently available on the market are getting smaller and smaller. Furthermore, there is a great variety of control methods and miniaturized control equipment available. For example, a number of revolutions of a rotary motor may be analyzed by a Hall-element just a few mm in size.

In accordance with another embodiment of the invention, the medical device comprises hydraulic means and the operation means comprises a pump for pumping a fluid in the hydraulic means, a motor for driving the pump, a valveless fluid conduit between the pump and the hydraulic means of the medical device, and a reservoir for fluid, wherein the reservoir forms part of the conduit. All of the hydraulic components involved are preferably devoid of any non-return valve. This is of great advantage, because with valves involved there is always a risk of malfunction due to improperly working valves, especially when long time periods passes between valve operations. The reservoir may form a fluid chamber with a variable volume, and the pump may distribute fluid from the chamber to the hydraulic means of the medical device by reduction of the volume of the chamber and withdraws fluid from the hydraulic means to the chamber by expansion of the volume of the chamber.

The control device may reverse the operation means by shifting polarity of the energy of the second form. Where the operation means comprises an electric motor the energy of the second form suitably comprises electric energy.

In accordance with yet another embodiment of the invention, the medical device is operable to perform a reversible function and there is an implantable reversing means for reversing the function performed by the medical device. Such a reversing function preferably is performed in a stepless manner. In this connection, the control device suitably controls the reversing means, which may include a switch, to reverse the function performed by the medical device. The reversing means may comprise hydraulic means including a valve for shifting the flow direction of a fluid in the hydraulic means. Alternatively, the reversing means may comprise a mechanical reversing means, such as a switch or a gearbox.

Where the reversing means comprises a switch the control device suitably controls the operation of the switch by shifting polarity of energy supplied to the switch. The switch may comprise an electric switch and the source of energy may supply electric energy for the operation of the switch.

In accordance with an advantageous embodiment of the invention, the apparatus further comprises an implantable energy storage means for storing the energy of the second form and for supplying energy in connection with the operation of the medical device. The energy storage means preferably comprises an electric source of energy, such as an accumulator, a rechargeable battery or a combination of an accumulator and rechargeable battery.

The apparatus may further comprise an implantable switch for switching the operation of the medical device and an implantable source of energy. This embodiment is particularly suited for applications where the energy transmission efficiency of the apparatus is insufficient, i.e. where the implanted medical device is to perform more advanced operations. Such a source of energy preferably is a battery. Alternatively, the source of energy is an accumulator which also may store the energy of the second form.

In accordance with a first alternative, the switch is operated by the energy of the second form supplied by the energy storage means to switch from an off mode, in which the source of energy is not in use, to an on mode, in which the source of energy supplies energy for the operation of the medical device. In this case, the implantable source of energy may comprise a battery, preferably having a life-time of at least 10 years, or an accumulator. However, other kinds of sources are also conceivable, such as a nuclear source of energy or a chemical source of energy.

In accordance with a second alternative, the apparatus further comprises a remote control for controlling the supply of energy of the implantable source of energy, wherein the switch is operated by the energy of the second form supplied by the energy storage means to switch from an off mode, in which the remote control is prevented from controlling the source of energy and the source of energy is not in use, to a standby mode, in which the remote control is permitted to control the source of energy to supply energy for the operation of the medical device.

In accordance with a third alternative, the energy storage means is omitted, wherein the switch is operated by the energy of the second form supplied by the energy transforming means to switch from an off mode, in which the remote control is prevented from controlling the source of energy and the source of energy is not in use, to a standby mode, in which the remote control is permitted to control the source of energy to supply energy for the operation of the medical device.

In accordance with a fourth alternative, also the remote control is omitted, wherein the switch is operated by the energy of the second form supplied by the energy transforming means to switch from an off mode, in which the source of energy is not in use, to an on mode, in which the source of energy supplies energy for the operation of the medical device. Where applicable, in the described embodiments the switch may switch when the energy transmission means is transmitting wireless energy, preferably while the transformed energy of the second form is stabilized by an implantable capacitor, which may temporarily (for a few seconds) store the energy of the second form.

The switch mentioned above may comprise an electronic switch or, where applicable, a mechanical switch.

The advantage of using a switch above all is increased control safety, i.e. interfering signals in the patient's surroundings cannot affect the implanted medical device. Furthermore, the lifetime of the source of energy will be significantly prolonged, since the energy consumption of the apparatus will be reduced to a minimum. During the above mentioned standby mode, the remote control uses energy from the source of energy. By means of the energy transmission means energy may be transmitted to activate the switch to connect the source of energy only when energy is required in connection with the operation of the medical device.

All of the above embodiments may be combined with at least one implantable sensor for sensing at least one physical parameter of the patient, wherein the control device may control the medical device in response to signals by the sensor. For example, the sensor may comprise a pressure sensor for directly or indirectly sensing the pressure against the medical device or human tissue. The pressure sensor may be any suitable known or conventional pressure sensor such as shown in U.S. Pat. Nos. 5,540,731, 4,846,181, 4,738,267, 4,571,749, 4,407,296 or 3,939,823; or an NPC-102 Medical Angioplasty Sensor. The control device may comprise an internal control unit to be implanted in the patient for, preferably directly, controlling the medical device in response to signals from the sensor. In response to signals from the sensor, for example pressure, the patient's position or any other important physical parameter, the internal control unit may send information thereon to outside the patient's body. The control device may also automatically control the medical device in response to signals from the sensor. For example, the control device may control the medical device in response to the sensor sensing that the patient is lying, or sensing an abnormally high pressure against the medical device.

Alternatively, the control device may comprise an external control unit outside the patient's body for, suitably directly, controlling the medical device in response to signals by the sensor. The external control unit may store information on the physical parameter sensed by the sensor and may be manually operated to control the medical device based on the stored information. In addition, there may be at least one implantable sender for sending information on the physical parameter sensed by the sensor.

An external data communicator may be provided outside the patient's body and an internal data communicator may be implanted in the patient for communicating with the external communicator. The implanted communicator may feed data related to the patient, or related to the implanted medical device, back to the external communicator. Alternatively or in combination, the external communicator may feed data to the internal communicator. The implanted communicator may suitably feed data related to at least one physical signal of the patient. The arrangement of external and internal communicators gives the advantage, among other things, that a long term control of activities related to the implanted medical device is achieved.

The apparatus may further comprise an implantable programmable control unit for controlling the medical device, preferably over time in accordance with an activity schedule program. This will advance the apparatus and make possible an adaptation of the apparatus to the individual patients.

All of the above embodiments are preferably remote controlled. Thus, the apparatus advantageously comprises a wireless remote control transmitting at least one wireless control signal for controlling the medical device. With such a remote control it will be possible to adapt the function of the apparatus to the patient's need in a daily basis, which is beneficial with respect to the treatment of the patient.

The wireless remote control may be capable of obtaining information on the condition of the implanted medical device and of controlling the medical device in response to the information. Also, The remote control may be capable of sending information related to the medical device from inside the patient's body to the outside thereof.

In a particular embodiment of the invention, the wireless remote control comprises at least one external signal transmitter or transceiver and at least one implantable internal signal receiver or transceiver. In another particular embodiment of the invention, the wireless remote control comprises at least one external signal receiver or transceiver and at least one implantable internal signal transmitter or transceiver.

The wireless remote control may transmit a carrier signal for carrying the control signal, wherein the carrier signal is frequency, amplitude or frequency and amplitude modulated and is digital, analog or digital and analog. Also the control signal used with the carrier signal may be frequency, amplitude or frequency and amplitude modulated.

The control signal may comprise a wave signal, for example, a sound wave signal, such as an ultrasound wave signal, an electromagnetic wave signal, such as an infrared light signal, a visible light signal, an ultra violet light signal, a laser signal, a micro wave signal, a radio wave signal, an x-ray radiation signal, or a gamma radiation signal. Where applicable, two or more of the above signals may be combined.

The control signal may be digital or analog, and may comprise an electric or magnetic field. Suitably, the wireless remote control may transmit an electromagnetic carrier wave signal for carrying the digital or analog control signal. For example, use of an analog carrier wave signal carrying a digital control signal would give safe communication. The control signal may be transmitted in pulses by the wireless remote control.

The energy transforming means may be placed in the thorax, abdomen or cephalic region, or implanted subcutaneous.

The energy transforming means of the apparatus may be implanted, for example subcutaneously, in the abdomen, thorax or cephal region, or other locations in the patient's body.

In accordance with a narrow aspect of the invention, the energy transforming means may be structurally different from the energy transmission means, and/or may transform the energy of the first form into the energy of the second form in a non-mechanical manner.

The medical implant apparatus as described above may be laparascopically implanted in a patient by placing at least two laparascopic cannula within the patient's body, and implanting the energy transforming means in the patient's body by using the at least two laparascopic cannula.

Alternatively the apparatus may be implanted by a) laparascopically placing a medical device of the apparatus through the abdomen or thorax of a patient, b) placing at least two laparoscopic trocars within the patient's body, c) using at least one dissecting tool inserted through the laparoscopic trocar, dissecting the region where the medical device is to be placed, d) introducing the medical device through the trocars, e) placing the medical device in engagement with an organ of the patient, and f) implanting an energy transforming means of the apparatus.

The method as recited in a)-e) may further comprise postoperatively adjusting the medical device in a non-invasive procedure.

It is the primary object of the present invention to provide a simple yet effective apparatus for treating chronic diseases in humans or animals. This and other objects of the invention will become clear from an inspection of the detailed description of the invention and from the appended claims.

The above described medical implant apparatus of the invention is suited for any of a variety of prior art implantable medical devices, such as infusion pumps for medication, transponders, pacemakers, heart stimulators, heart sensors, rings or cuffs for sphincter function used for urinary and anal incontinence, medical devices implanted in penis for treating impotence, rings or cuffs for sphincter function used for occluding a blood vessel, for example a penis vein of an impotent patient, gastric bands, hiatus hernia treatment devices, equipment for analyzing body functions or blood parameters, and stimulators for generating electric pulses.

The present invention is described in more detail in the following with reference to the accompanying drawings in which FIGS. 1 to 12 are schematic block diagrams illustrating twelve embodiments, respectively, of the medical implant apparatus of the invention, in which wireless energy is transmitted from outside a patient's body to energy consuming components of the apparatus implanted in the patient;

Figure 1:
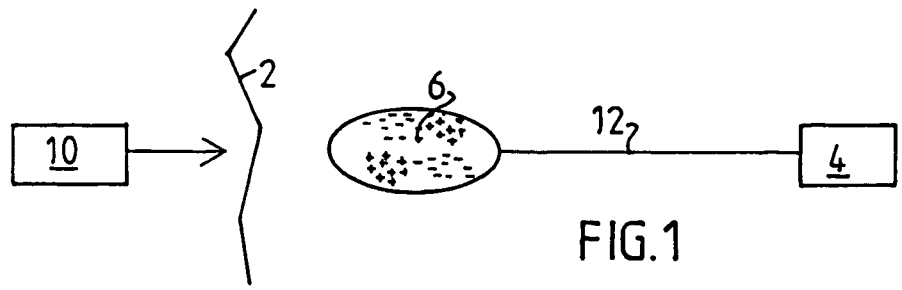

FIG. 1 schematically shows a very simple embodiment of the medical implant apparatus of the invention having some parts implanted in a patient and other parts located outside the patient's body. Thus, in FIG. 1 all parts placed to the right of the patient's skin 2 are implanted and all parts placed to the left of the skin 2 are located outside the patient's body.

The apparatus of FIG. 1 comprises an implanted operable medical device 4, which engages a lumen of an organ of the patient to form a restricted passageway in the lumen. Such a lumen may comprise the esophagus, urethra, rectum, colon, a blood vessel or the like. The medical device 4 is capable of performing a reversible function, i.e. to enlarge and reduce the cross-sectional area of the passageway, so that the medical device 4 works as an artificial sphincter. An implanted energy transforming means 6 is adapted to supply energy consuming components of the medical device 4 with energy via a power supply line 12. An external energy transmission means 10 includes a wireless remote control transmitting a wireless signal which is received by a signal receiver incorporated in the implanted energy transforming means 6. The implanted energy transforming means 6 transforms energy from the signal into electric energy which is supplied via the power supply line 12 to the medical device 4, which energy causes portions of the device 4 to move and thus adjust the passageway.

Figure 2:
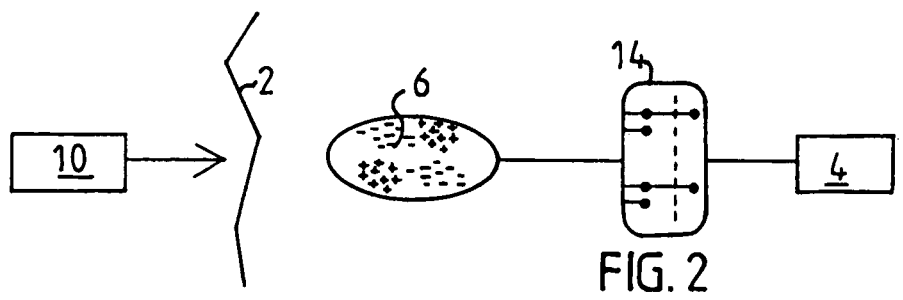

FIG. 2 shows an embodiment of the invention identical to that of FIG. 1, except that a reversing means in the form of an electric switch 14 also is implanted in the patient for reversing the medical device 4. The wireless remote control of the external energy transmission means 10 transmits a wireless signal that carries energy and the implanted energy transforming means 6 transforms the wireless energy into a current for operating the switch 14. When the polarity of the current is shifted by the energy transforming means 6 the switch 14 reverses the function performed by the medical device 4.

Figure 3:
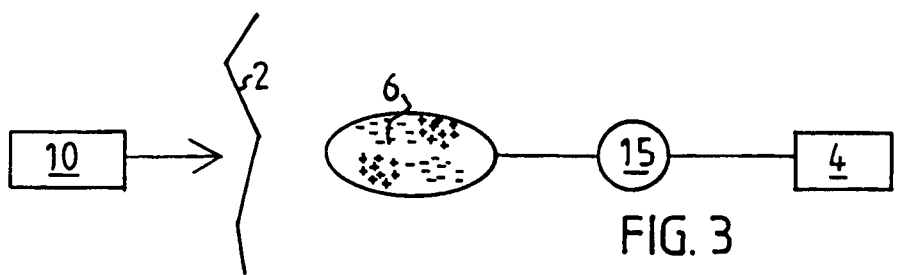

FIG. 3 shows an embodiment of the invention identical to that of FIG. 1, except that an operation means in the form of a motor 15 for operating the medical device 4 also is implanted in the patient. The motor 15 is powered with energy from the energy transforming means 6, as the remote control of the external energy transmission means 10 transmits a wireless signal to the receiver of the energy transforming means 6.

Figure 4:
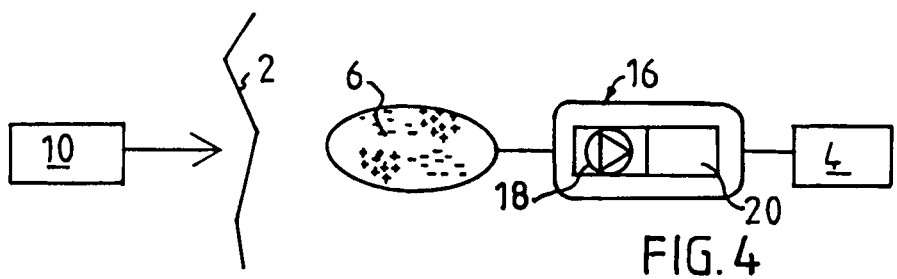

FIG. 4 shows an embodiment of the invention identical to that of FIG. 1, except that an assembly 16 including a motor/pump unit 18 and a fluid reservoir 20 also is implanted in the patient. In this case the medical device 4 is hydraulically operated, i.e. hydraulic fluid is pumped by the motor/pump unit 18 from the reservoir 20 through a conduit 22 to the medical device 4 to reduce the cross-sectional area of the passageway, and hydraulic fluid is pumped by the motor/pump unit 18 back from the medical device 4 to the reservoir 20 to enlarge the cross-sectional area. The implanted energy transforming means unit 6 transforms wireless energy into a current for powering the motor/pump unit 18 via an electric power supply line 24.

Figure 5:
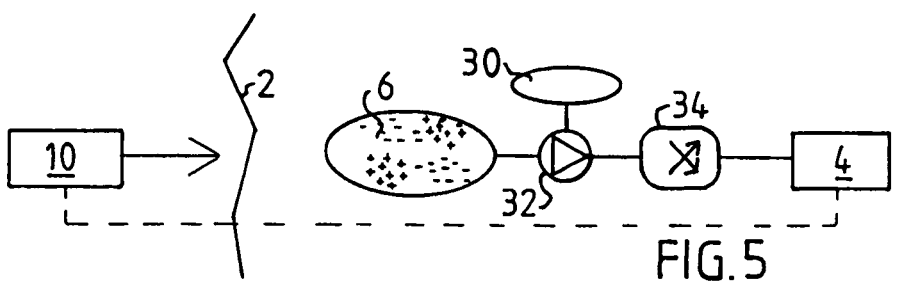

FIG. 5 shows an embodiment of the invention comprising the external energy transmission means 10 with its wireless remote control, the medical device 4, in this case hydraulically operated, and the implanted energy transforming means 6, and further comprising an implanted hydraulic fluid reservoir 30, an implanted motor/pump unit 32 and an implanted reversing means in the form of a hydraulic valve shifting device 34. The motor of the motor/pump unit 32 is an electric motor. In response to a control signal from the wireless remote control of the external energy transmission means 10, the implanted energy transforming means 6 powers the motor/pump unit 32 with energy from the energy carried by the control signal, whereby the motor/pump unit 32 distributes hydraulic fluid between the reservoir 30 and the medical device 4. The remote control of the energy transmission means 10 controls the shifting device 34 to shift the hydraulic fluid flow direction between one direction in which the fluid is pumped by the motor/pump unit 32 from the reservoir 30 to the medical device 4 to reduce the cross-sectional area of the passageway, and another opposite direction in which the fluid is pumped by the motor/pump unit 32 back from the medical device 4 to the reservoir 30 to enlarge the cross-sectional area.

Figure 6:
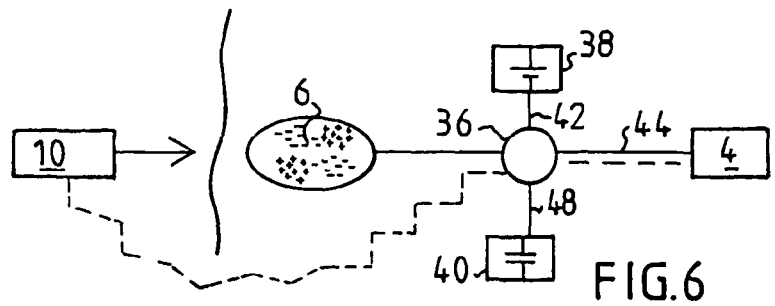

FIG. 6 shows an embodiment of the invention identical to that of FIG. 1, except that a control unit 36 controlled by the wireless remote control of the external energy transmission means 10, an accumulator 38 and a capacitor 40 also are implanted in the patient. The control unit 36 stores electric energy received from the energy transforming means 6 in the accumulator 38, which supplies energy to the medical device 4. In response to a control signal from the wireless remote control of the energy transmission means 10, the control unit 6 either releases electric energy from the accumulator 38 and transfers the released energy via power lines 42 and 44, or directly transfers electric energy from the energy transforming means 6 via a power line 46, the capacitor 40, which stabilizes the electric current, a power line 48 and the power line 44, for the operation of the medical device 4.

In accordance with one alternative, the capacitor 40 in the embodiment of FIG. 6 may be omitted. In accordance with another alternative, the accumulator 38 in this embodiment may be omitted.

Figure 7:
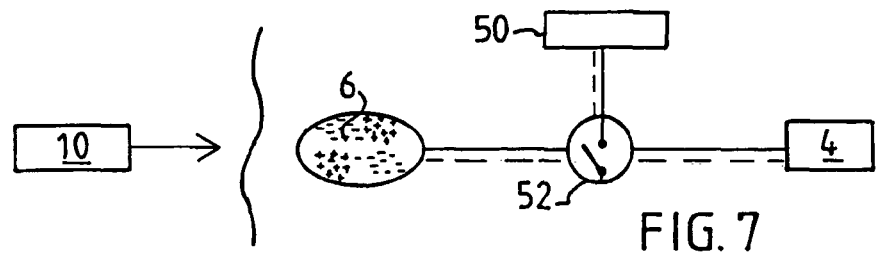

FIG. 7 shows an embodiment of the invention identical to that of FIG. 1, except that a battery 50 for supplying energy for the operation of the medical device 4 and an electric switch 52 for switching the operation of the medical device 4 also are implanted in the patient. The switch 52 is operated by the energy supplied by the energy transforming means 6 to switch from an off mode, in which the battery 50 is not in use, to an on mode, in which the battery 50 supplies energy for the operation of the medical device 4.

Figure 8:
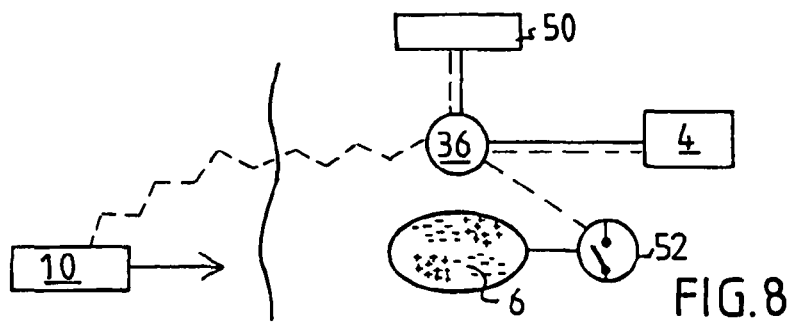

FIG. 8 shows an embodiment of the invention identical to that of FIG. 7, except that a control unit 36 controllable by the wireless remote control of the external energy transmission means 10 also is implanted in the patient. In this case, the switch 52 is operated by the energy supplied by the energy transforming means 6 to switch from an off mode, in which the wireless remote control is prevented from controlling the control unit 36 and the battery is not in use, to a standby mode, in which the remote control is permitted to control the control unit 36 to release electric energy from the battery 50 for the operation of the medical device 4.

Figure 9:
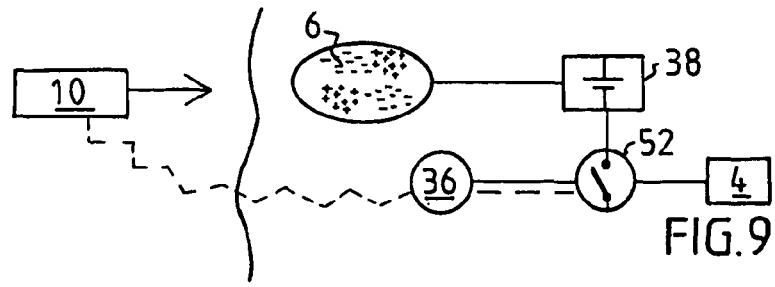

FIG. 9 shows an embodiment of the invention identical to that of FIG. 8, except that an accumulator 38 is substituted for the battery 50 and the implanted components are interconnected differently. In this case, the accumulator 38 stores energy from the energy transforming means 6. In response to a control signal from the wireless remote control of the external energy transmission means 10, the implanted control unit 36 controls the switch 52 to switch from an off mode, in which the accumulator 38 is not in use, to an on mode, in which the accumulator 38 supplies energy for the operation of the medical device 4.

Figure 10:
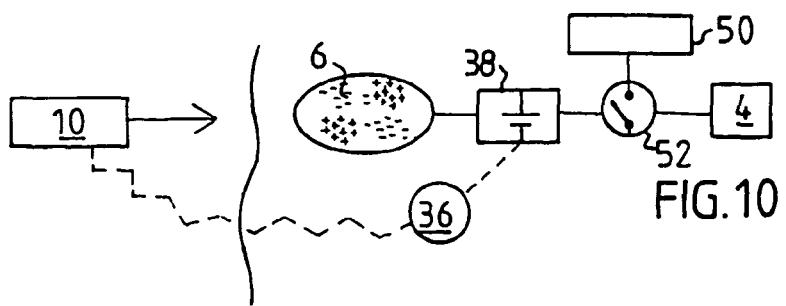

FIG. 10 shows an embodiment of the invention identical to that of FIG. 9, except that a battery 50 also is implanted in the patient and the implanted components are interconnected differently. In response to a control signal from the wireless remote control of the external energy transmission means 10, the implanted control unit 36 controls the accumulator 38 to deliver energy for operating the switch 52 to switch from an off mode, in which the battery 50 is not in use, to an on mode, in which the battery 50 supplies electric energy for the operation of the medical device 4.

Alternatively, the switch 52 may be operated by energy supplied by the accumulator 38 to switch from an off mode, in which the wireless remote control is prevented from controlling the battery 50 to supply electric energy and is not in use, to a standby mode, in which the wireless remote control is permitted to control the battery 50 to supply electric energy for the operation of the medical device 4.

Figure 11:
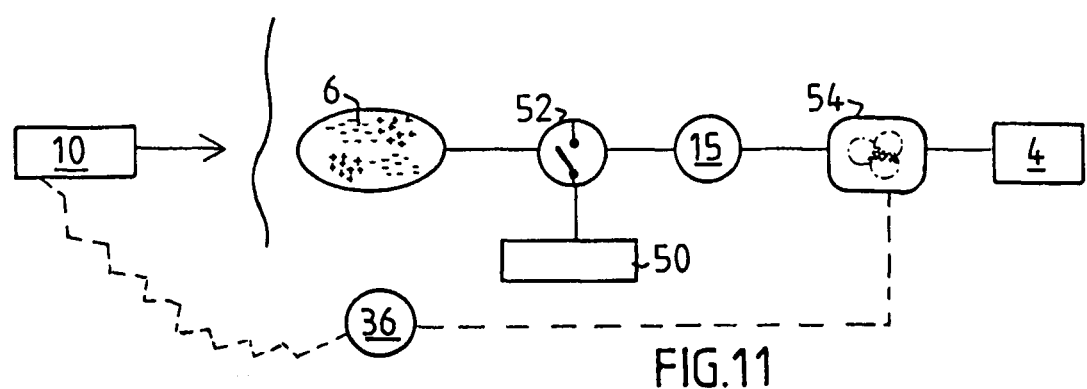

FIG. 11 shows an embodiment of the invention identical to that of FIG. 7, except that a motor 15, a mechanical reversing means in the form of a gearbox 54, and a control unit 36 for controlling the gearbox 54 also are implanted in the patient. The implanted control unit 36 controls the gearbox 54 to reverse the function performed by the medical device 4 (mechanically operated).

Figure 12:
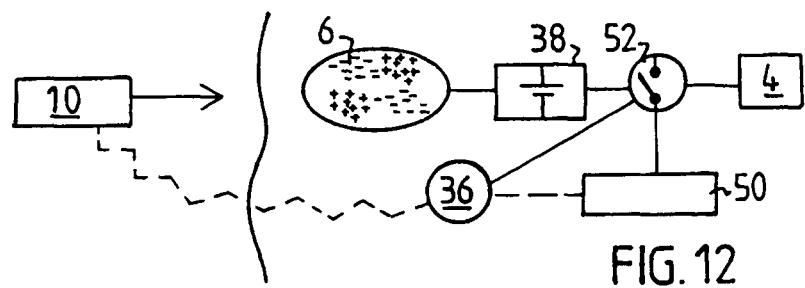

FIG. 12 shows an embodiment of the invention identical to that of FIG. 10 except that the implanted components are interconnected differently. Thus, in this case the control unit 36 is powered by the battery 50 when the accumulator 38, suitably a capacitor, activates the switch 52 to switch to an on mode. When the switch 52 is in its on mode the control unit 36 is permitted to control the battery 50 to supply, or not supply, energy for the operation of the medical device 4.

Figure 13:
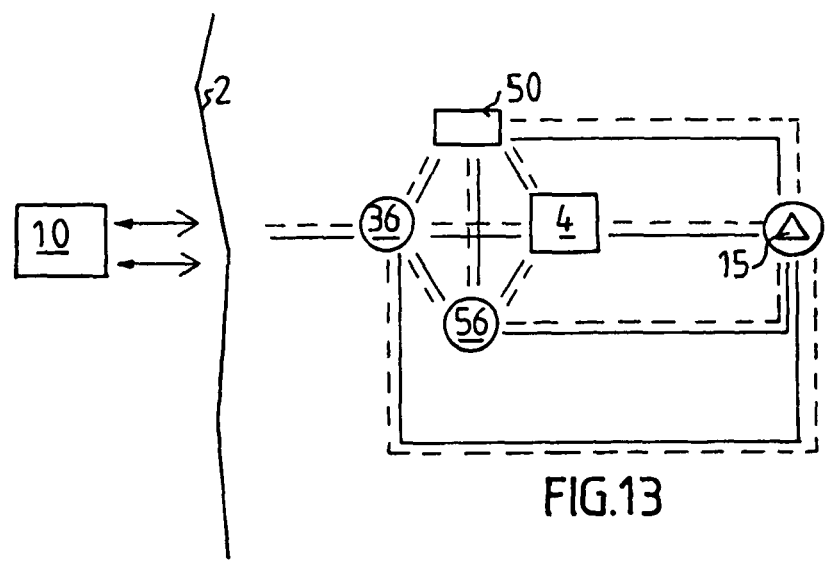
FIG. 13 is a schematic block diagram illustrating conceivable combinations of implanted components for achieving various communication options.

FIG. 13 schematically shows conceivable combinations of implanted components of the apparatus for achieving various communication options. Basically, there are the implanted medical device 4, control unit 36 and motor/pump unit 18, and the external energy transmission means 10 including the external wireless remote control. As already described above the wireless remote control transmits a control signal which is received by the implanted control unit 36, which in turn controls the various implanted components of the apparatus.

A sensor 56 may be implanted in the patient for sensing a physical parameter of the patient, such as the pressure in the passageway. The implanted control unit 36, or alternatively the external wireless remote control of the energy transmission means 10, may control the medical device 4 in response to signals from the sensor 56. A transceiver may be combined with the sensor 56 for sending information on the sensed physical parameter to the external wireless remote control. The wireless remote control may comprise a signal transmitter or transceiver and the implanted control unit 36 may comprise a signal receiver or transceiver. Alternatively, the wireless remote control may comprise a signal receiver or transceiver and the implanted control unit 36 may comprise a signal transmitter or transceiver. The above transceivers, transmitters and receivers may be used for sending information or data related to the medical device 4 from inside the patient's body to the outside thereof.

Where the motor/pump unit 18 and battery 50 for powering the motor/pump unit 18 are implanted, the battery 50 may be equipped with a transceiver for sending information on the condition of the battery 50.

Those skilled in the art will realize that the above various embodiments according to FIGS. 1-13 could be combined in many different ways. For example, the energy operated switch 14 could be incorporated in any of the embodiments of FIGS. 3,6-12, the hydraulic shifting device 34 could be incorporated in the embodiment of FIG. 4, and the gearbox 54 could be incorporated in the embodiment of FIG. 3.

Figure 14:
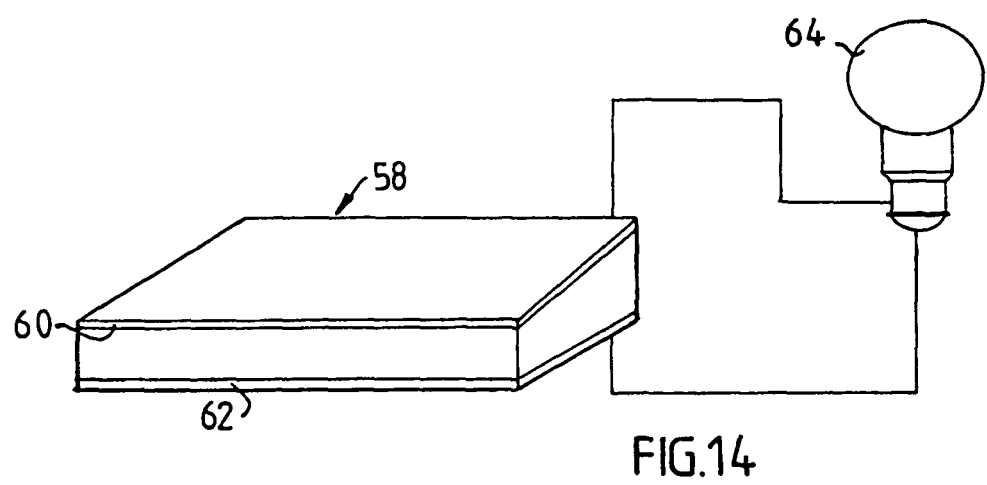
FIG. 14 illustrates an electrical junction element for use in the apparatus of the present invention.

FIG. 14 shows an energy transforming means in the form of an electrical junction element 58 for use in any of the above embodiments according to FIGS. 1-13. The element 58 is a flat p-n junction element comprising a p-type semiconductor layer 60 and an n-type semiconductor layer 62 sandwiched together. A light bulb 64 is electrically connected to opposite sides of the element 58 to illustrate how the generated current is obtained.

The output of current from such a p-n junction element 58 is correlated to the temperature. See the formula below.

$$I = I0(\exp(qV/kT) - 1)$$

where

I is the external current flow,

I0 is the reverse saturation current, q is the fundamental electronic charge of 1.602×10-19 coulombs, V is the applied voltage, k is the Boltzmann constant, and T is the absolute temperature.

Under large negative applied voltage (reverse bias), the exponential term becomes negligible compared to 1.0, and I is approximately −I0. I0 is strongly dependent on the temperature of the junction and hence on the intrinsic-carrier concentration. I0 is larger for materials with smaller bandgaps than for those with larger bandgaps. The rectifier action of the diode—that is, its restriction of current flow to only one direction—is in this particular embodiment the key to the operation of the p-n junction element 58.

An alternative way to design a p-n junction element is to deposit a thin layer of semiconductor onto a supporting material which does not absorb the kind of energy utilized in the respective embodiments. For use with wirelessly transmitted energy in terms of light waves, glass could be a suitable material. Various materials may be used in the semiconductor layers such as but not limited to cadmium telluride, copper-indium-diselenide and silicon. It is also possible to use a multilayer structure with several layers of p and n-type materials to improve efficiency.

The electric energy generated by the p-n junction element 58 could be of the same type as generated by solar cells, in which the negative and positive fields create a direct current. Alternatively, the negative and positive semiconductor layers may change polarity following the transmitted waves, thereby generating an alternating current.

The p-n junction element 58 is designed to make it suited for implantation. Thus, all the external surfaces of the element 58 in contact with the human body are made of a biocompatible material. The p-n junction semiconductors are designed to operate optimally at a body temperature of 37° C. because the current output, which should be more than 1 μA, is significantly depending on temperature as shown above. Since both the skin and subcutis absorb energy, the relation between the sensitivity or working area of the element 58 and the intensity or strength of the wireless energy transmission is considered. The p-n junction element 58 preferably is designed flat and small. Alternatively, if the element 58 is made in larger sizes it should be flexible, in order to adapt to the patient's body movements. The volume of the element 58 should be kept less than 2000 cm$^3$.

Figure 15:
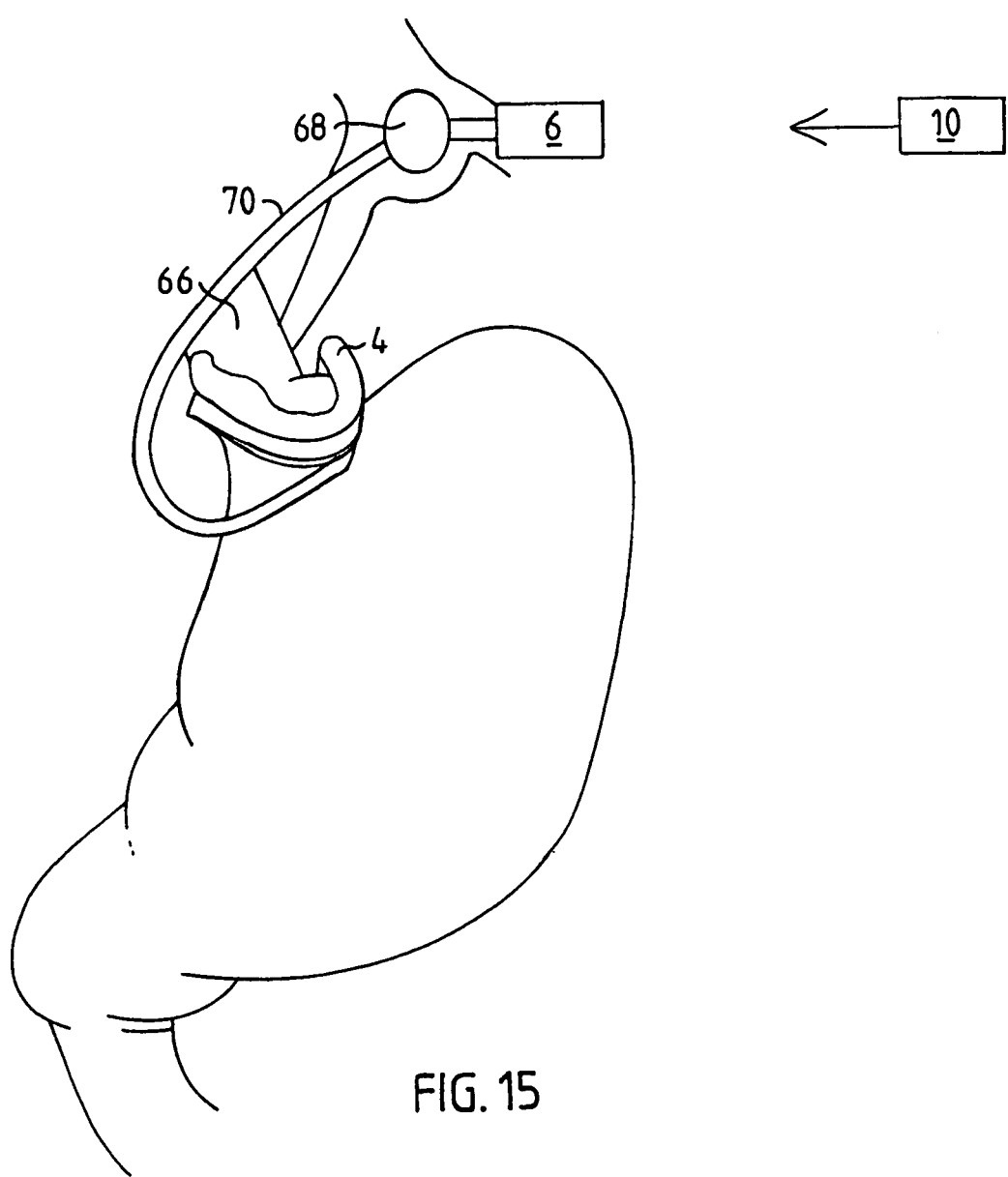
FIG. 15 illustrates an example of the apparatus in accordance with the invention, in which a medical device is implanted in a patient for treating heartburn and reflux disease.

FIG. 15 illustrates how any of the above-described embodiments of the medical implant apparatus of the invention may be implanted in a patient for treating heartburn and reflux disease. Thus, a medical device 4 implanted in a patient engages the esophagus 66 close to the cardia to form an artificial sphincter around the food passageway in the esophagus. An implanted operation means 68, which may also be referred to as an adjustment means, such as an electric motor or a motor/pump assembly, operates the medical device 4 through a transmission member 70, such as a mechanical transmission cord or a fluid tube. An energy transforming means in the form of an element 6 having a positive region and a negative region, as described above in more detail, is placed underneath the skin of the patient.

Wireless energy carried by a signal transmitted by a wireless remote control of an external energy transmission means 10 at least partly penetrates the patient's skin and hits the element 6. The energy thus hitting the element 6 is transformed into energy of a different form that is suited for powering the operation means 68. For example, where the operation means 68 is an electric motor the element 6 comprises an electric p-n junction element that transforms the wireless energy into an electric current for powering the electric motor. Where the operation means 68 comprises a pump, the element 6 may transform the wireless energy into kinetic energy for powering the pump.

The transformed energy may be utilized for directly operating the medical device 4 or, where the medical device 4 is electrically operated, for storage in a capacitor and/or an accumulator for later or parallel use. Preferably (but not necessarily) the element 6 is controlled by a microprocessor. The wireless remote control of the external energy transmission means 10 is used to control the utilization of the transmitted energy and any function or command to/from the implanted medical device 4.

The invention claimed is:

1. A medical implant apparatus for a patient, comprising: an energy transmission means for wireless transmission of energy of a first form from outside the patient's body; an implantable medical device operable in response to energy of a second form; and an implantable energy transforming means for transforming the energy of the first form wirelessly transmitted by the energy transmission means into energy of the second form, which is used for operating the medical device, wherein the energy transforming means comprises at least one element having a positive region and a negative region and adapted to create an energy field between said positive and negative region when exposed to wireless energy of the first form transmitted by the energy transmission means, so that the energy field produces energy of the second form, wherein the element comprises an electrical semi-conductor junction element capable of inducing an electric field between the positive and negative regions when exposed to energy of the first form transmitted by the energy transmission means, wherein the electrical semi-conductor junction element comprises a flat sheet, and wherein the electrical semi-conductor junction element is adapted to generate an electrical current whereby the energy of the second form comprises electric energy, wherein the medical device is electrically operated, and the positive and negative regions of the electrical semi-conductor junction element supply electric energy for the operation of the medical device, the medical implant further comprising an implantable motor, pump or motor and pump operably connected to the medical device, wherein the element is adapted to power the implantable motor, pump or motor and pump with energy of the second form, by at least one of:

directly operating, with the energy of the second form as the energy transmission means transmits energy of the first form, and storing energy in a comprised implantable energy storage device being an electric accumulator, the electric accumulator comprising at least one capacitor or battery for storing energy of the second form for indirect supply of energy.

2. The apparatus according to claim 1, wherein energy of the second form used for operating the medical device is wirelessly transmitted by the energy transforming means.

3. An apparatus according to claim 1, further comprising electric conductors connected to the positive and negative regions of the electrical junction element, whereby the electrical junction element is capable of supplying an electric current via the electric conductors.

4. An apparatus according to claim 3, wherein the electrical junction element is capable of supplying a direct current or pulsating direct current via the conductors.

5. An apparatus according to claim 3, wherein the electrical junction element is capable of supplying an alternating current or a combination of a direct and alternating current via the conductors.

6. An apparatus according to claim 1, wherein the electrical junction element is capable of supplying a frequency or amplitude modulated signal.

7. An apparatus according to claim 1, wherein the electrical junction element is capable of supplying an analog or digital signal.

8. An apparatus according to claim 1, further comprising an implantable pulse generator for generating electrical pulses from energy of the second form produced by the energy field.

9. An apparatus according to claim 1, wherein the electrical junction element generates an output current exceeding 1 µA when exposed to energy of the first form transmitted by the energy transmission means.

10. An apparatus according to claim 1, wherein the electrical junction element forms a flat sheet, and has a volume of less than 2000 cm$^3$.

11. An apparatus according to claim 1, wherein the energy transforming means comprises at least one semiconductor circuitry having the positive region and the negative region, and adapted to create an, energy field between the positive and negative regions when exposed to energy of the first form transmitted by the energy transmission means, so that the energy field produces energy of the second form.

12. An apparatus according to claim 1, wherein the energy transforming means comprises at least one transistor circuitry having the positive region and the negative region, and adapted to create an energy field between the positive and negative regions when exposed to energy of the first form transmitted by the energy transmission means, so that the energy field produces energy of the second form.

13. An apparatus according to claim 1, wherein the energy transforming means comprises at least one microchip having the positive region and the negative region, and adapted to create an energy field between the positive and negative regions when exposed to energy of the first form transmitted by the energy transmission means, so that the energy field produces energy of the second form.

14. An apparatus according to claim 1, wherein the medical device is electrically operated, the energy transforming means is functionally different from the energy transmission means and is adapted to transform energy of the first form into electric energy, and the implantable energy storage device comprises an electric energy storage means for storing the electric energy from the energy transforming means and for supplying electric energy for operation of the medical device.

15. An apparatus according to claim 14, wherein the energy transforming means is capable of inducing an electric field between the positive and negative regions when exposed to energy of the first form transmitted by the energy transmission means, the positive and negative regions of the electrical junction element being electrically connected to the electric energy means.

16. An apparatus according to claim 1, further comprising an implantable switch operable by energy of the second form supplied by the implantable energy storage device to switch from an off mode, in which the implantable energy storage device is not in use, to an on mode, in which the implantable energy storage device supplies energy for the operation of the medical device.

17. An apparatus according to claim 1, further comprising a remote control for controlling the supply of energy from the implantable energy storage device, and an implantable switch operable by energy of the second form supplied by the implantable energy storage device to switch from an off mode, in which the remote control is prevented from controlling the implantable energy storage device and the implantable energy storage device is not in use, to a standby mode, in which the remote control is permitted to control the implantable energy storage device to supply energy for the operation of the medical device.

18. An apparatus according to claim 1, further comprising an implantable switch operable by energy of the second form supplied by the energy transforming means to switch from an off mode, in which the implantable energy storage device is not in use, to an on mode, in which the implantable energy storage device supplies energy for the operation of the medical device.

19. An apparatus according to claim 1, further comprising a remote control for controlling supply of energy from the implantable energy storage device, and an implantable switch operable by energy of the second form supplied by the energy transforming means to switch from an off mode, in which the remote control is prevented from controlling the implantable energy storage device and the implantable energy storage device is not in use, to a standby mode, in which the remote control is permitted to control the implantable energy storage device to supply energy for the operation of the medical device.

20. An apparatus according to claim 1, wherein the energy transmission means transmits energy of the first form by at least one wireless signal.

21. An apparatus according to claim 20, wherein the at least one wireless signal comprises a wave signal.

22. An apparatus according to claim 21, wherein the at least one wireless signal contains radiant energy.

23. An apparatus according to claim 21, wherein the wave signal comprises electromagnetic waves including one of infrared light, visible light, ultra violet light, laser light, micro waves, radio waves, x-ray radiation, and gamma radiation.

24. An apparatus according to claim 21, wherein the wave signal comprises sound waves.

25. An apparatus according to claim 20, wherein the at least one wireless signal comprises a digital or analog signal.

26. An apparatus according to claim 1, wherein energy of the first form transmitted by the energy transmission means comprises an electric field.

27. An apparatus according to claim 26, wherein the electric field is transmitted in pulses or digital pulses by the energy transmission means.

28. An apparatus according to claim 1, wherein energy of the first form transmitted by the energy transmission means comprises a magnetic field.

29. An apparatus according to claim 28, wherein the magnetic field is transmitted in pulses or digital pulses by the energy transmission means.

30. An apparatus according to claim 1, further comprising a wireless remote control transmitting at least one wireless control signal for controlling the medical device.

31. An apparatus according to claim 30, wherein the remote control is capable of obtaining information on a condition of the implantable medical device and to control the medical device in response to the information.

32. An apparatus according to claim 30, wherein the remote control comprises an implanted control unit for controlling the medical device.

33. An apparatus according to claim 32, wherein the control unit comprises a microprocessor.

34. An apparatus, according to claim 30, wherein the wireless remote control comprises at least one external signal transmitter or transceiver and at least one implantable internal signal receiver or transceiver.

35. An apparatus according to claim 30, wherein the wireless remote control comprises at least one external signal receiver or transceiver and at least one implantable internal signal transmitter or transceiver.

36. An apparatus according to claim 30, wherein the remote control is capable of sending information related to the medical device from inside the patient's body to the outside thereof.

37. An apparatus according to claim 31, wherein the remote control controls the medical device in response to the information.

38. An apparatus according to claim 30, wherein the remote control comprises a control signal transmitter for transmitting the at least one wireless control signal, and the energy transmission means comprises the control signal transmitter, whereby energy of the first form is transmitted by the at least one wireless control signal.

39. An apparatus according to claim 30, wherein the energy transmission means transmits energy of the first form by at least one signal separate from the at least one wireless control signal.

40. An apparatus according to claim 30, wherein the remote control transmits a carrier signal for carrying the at least one wireless control signal.

41. An apparatus according to claim 30, wherein the energy transmission means transmits energy of the first form by at least one signal, which is used as a carrier signal for the at least one wireless control signal transmitted by the remote control.

42. An apparatus according to claim 40, wherein the carrier signal is frequency or amplitude modulated.

43. An apparatus according to claim 40, wherein the carrier signal comprises digital or analog waves.

44. An apparatus according to claim 40, wherein the at least one wireless control signal used with the carrier signal is frequency or amplitude modulated.

45. An apparatus according to claim 40, wherein the at least one wireless control signal used with the carrier signal is digital or analog.

46. An apparatus according to claim 30, wherein the at least one wireless control signal comprises a wave signal comprising one of a sound wave signal including an ultrasound wave signal, an electromagnetic wave signal including an infrared light signal, a visible light signal, an ultra violet light signal and a laser light signal, a micro wave signal, a radio wave signal, an x-ray radiation signal, and a gamma radiation signal.

47. An apparatus according to claim 30, wherein the at least one wireless control signal comprises an electric or magnetic field.

48. An apparatus according to claim 30, wherein the at least one wireless control signal comprises a digital or analog control signal.

49. An apparatus according to claim 48, wherein the remote control transmits an electromagnetic carrier wave signal for carrying the digital or analog control signal.

50. An apparatus according to claim 1, wherein the energy transforming means transforms energy of the first form into a direct current or pulsating direct current.

51. An apparatus according to claim 1, wherein the energy transforming means transforms energy of the first form into an alternating current or a combination of a direct and alternating current.

52. An apparatus according to claim 1, wherein the energy of the second form comprises a frequency or amplitude modulated signal.

53. An apparatus according to claim 1, wherein the energy of the second form comprises an analog or a digital signal.

54. An apparatus according to claim 1, further comprising an implantable control unit for controlling the medical device.

55. An apparatus according to claim 54, wherein the control unit is programmable for controlling the medical device over time, and wherein the control unit controls the medical device over time in accordance with an activity schedule program.

56. An apparatus according to claim 55, further comprising an external wireless remote control for programming the control unit.

57. An apparatus according to claim 54, further comprising an implantable sensor for sensing a physical parameter of the patient.

58. An apparatus according to claim 57, wherein the control unit controls the medical device in response to signals by the sensor.

59. An apparatus according to claim 58, wherein the control unit directly controls the medical device in response to signals by the sensor.

60. An apparatus according to claim 57, further comprising an external control unit outside the patient's body, wherein the external control unit controls the medical device in response to signals by the sensor.

61. An apparatus according to claim 1, wherein the energy of the first form comprises polarized energy.

62. An apparatus according to claim 1, further comprising an implantable pulse generator for generating electrical pulses from energy of the second form.

63. An apparatus according to claim 1, further comprising at least one implantable sensor for sensing at least one physical parameter of the patient, and an implantable sender for sending information on the at least one physical parameter sensed by the sensor.

64. An apparatus according to claim 1, further comprising an external data communicator and an implantable internal data communicator communicating with the external data communicator, wherein the internal data communicator feeds data related to the medical device back to the external data communicator or the external communicator feeds data to the internal data communicator.

65. An apparatus according to claim 64, wherein the internal data communicator feeds data related to at least one physical signal of the patient.

66. An apparatus according to claim 1, further comprising a switch for directly or indirectly switching supply of energy of the second form for the operation of the medical device.

67. An apparatus according to claim 1, further comprising implantable hydraulic means for operating the medical device, and at least one valve for controlling a fluid flow in the hydraulic means.

68. An apparatus according to claim 67, further comprising a wireless remote control for controlling the at least one valve.

69. An apparatus according to claim 1, wherein the medical device is adapted to control the size of a through-flow area of a lumen formed by an organ of the patient.

70. An apparatus according to claim 1, wherein the medical device is non-inflatable.

71. An apparatus according to claim 1, further comprising an implantable operation means for operating the medical device, wherein the medical device comprises hydraulic means, the operation means comprises a reservoir forming a fluid chamber with a variable volume connected to the hydraulic means, and the operation means distributes fluid from the chamber to the hydraulic means by reduction of the volume of the chamber and withdraws fluid from the hydraulic means to the chamber by expansion of the volume of the chamber.

72. An apparatus according to claim 1, further comprising an operation means for operating the medical device and a control device for controlling the operation means.

73. An apparatus according to claim 72, wherein the control device shifts polarity of energy of the second form to reverse the operation means.

74. An apparatus according to claim 73, wherein the operation means comprises an electric motor and energy of the second form comprises electric energy.

75. An apparatus according to claim 72, wherein the medical device is operable to perform a reversible function.

76. An apparatus according to claim 75, further comprising an implantable reversing means for reversing the function performed by the medical device.

77. An apparatus according to claim 76, wherein a control device controls the reversing means to reverse the function performed by the medical device.

78. An apparatus according to claim 76, wherein the reversing means comprises hydraulic means including a valve for shifting the flow direction of a fluid flow in the hydraulic means.

79. An apparatus according to claim 76, wherein the reversing means comprises a mechanical reversing means.

80. An apparatus according to claim 79, wherein the reversing means comprises a gearbox.

81. An apparatus according to claim 76, wherein the reversing means comprises a switch.

82. An apparatus according to claim 81, wherein the control device controls operation of the switch by shifting polarity of energy supplied to the switch.

83. An apparatus according to claim 82, wherein the switch comprises an electric switch and the implantable energy storage device supplies electric energy for the operation of the switch.

84. An apparatus according to claim 72, wherein the operation means comprises a motor.

85. An apparatus according to claim 84, wherein the motor comprises a rotary motor, and the control device controls the rotary motor to rotate a desired number of revolutions.

86. An apparatus according to claim 84, wherein the motor comprises a linear motor.

87. An apparatus according to claim 84, wherein the motor comprises a hydraulic or pneumatic fluid motor, and the control device controls the fluid flow through the hydraulic or pneumatic fluid motor.

88. An apparatus according to claim 84, wherein the motor comprises an electric motor having electrically conductive parts made of plastics.

89. An apparatus according to claim 1, further comprising an implantable operation means for operating the medical device, wherein the medical device comprises hydraulic means and the operation means comprises the pump, and wherein the pump is a pump for pumping a fluid in the hydraulic means.

90. An apparatus according to claim 89, wherein the operation means comprises a motor for driving the pump.

91. An apparatus according to claim 90, wherein the operation means comprises a fluid conduit between the pump and the hydraulic means of the medical device, and a reservoir for fluid, the reservoir forming part of the conduit.

92. An apparatus according to claim 91, wherein the conduit is devoid of any non-return valve.

93. An apparatus according to claim 91, wherein the reservoir forms a fluid chamber with a variable volume, and the pump distributes fluid from the chamber to the hydraulic means of the medical device by reduction of the volume of the chamber and withdraws fluid from the hydraulic means to the chamber by expansion of the volume of the chamber.

94. An apparatus according to claim 1, further comprising an implantable control unit for controlling the medical device, wherein the control unit comprises, a microprocessor.

95. The medical implant apparatus according to claim 1, wherein the medical device is directly operated with energy of the second form, as the energy transmission means transmits energy of the first form.

96. An apparatus according to claim 95, wherein the medical device is directly operated with energy of the second form in a non-magnetic manner.

97. An apparatus according to claim 95, wherein the medical device is directly operated with energy of the second form in a non-mechanical manner.

98. An apparatus according to claim 1, wherein the energy transforming means is adapted to be implanted subcutaneously or in the abdomen of the patient.

99. An apparatus according to claim 1, wherein the energy transforming means is adapted to be implanted in the thorax or in the cephal region of the patient.

100. An apparatus according to claim 1, wherein the energy transforming means is adapted to be implanted in an orifice of the patient's body and under the mucosa or intraluminar outside the mucosa of the orifice.

101. An apparatus according to claim 1, wherein parts of the energy transforming means capable of being in contact with the patient when implanted are made of biocompatible material.

102. An apparatus according to claim 1, wherein the energy transforming means is structurally different, from the energy transmission means.

103. An apparatus according to claim 1, wherein the energy transforming means is adapted to transform the energy of the first form into the energy of the second form in a non-mechanical manner.

* * * * *